(12) United States Patent
Keith (10) Patent No.: US 10,466,247 B2
(45) Date of Patent: Nov. 5, 2019

(54) SYSTEM AND METHOD FOR DIAGNOSING SENSOR PERFORMANCE USING ANALYTE-INDEPENDENT RATIOMETRIC SIGNALS

(71) Applicant: Becton, Dickinson and Company, Franklin Lakes, NJ (US)

(72) Inventor: Steven Keith, Chapel Hill, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1244 days.

(21) Appl. No.: 13/828,601

(22) Filed: Mar. 14, 2013

(65) Prior Publication Data

US 2014/0141524 A1 May 22, 2014

Related U.S. Application Data

(60) Provisional application No. 61/728,488, filed on Nov. 20, 2012.

(51) Int. Cl.
  *G01N 33/52* (2006.01)
  *G01N 33/66* (2006.01)
  *G01N 21/64* (2006.01)

(52) U.S. Cl.
  CPC ......... *G01N 33/66* (2013.01); *G01N 21/6428* (2013.01); *G01N 33/52* (2013.01)

(58) Field of Classification Search
  None
  See application file for complete search history.

(56) References Cited

U.S. PATENT DOCUMENTS

| | | |
|---|---|---|
| 5,094,958 A | 3/1992 | Klainer et al. |
| 5,409,835 A | 4/1995 | Lakowicz et al. |
| 5,605,152 A | 2/1997 | Slate et al. |
| 5,624,847 A | 4/1997 | Lakowicz et al. |
| 5,628,310 A | 5/1997 | Rao et al. |
| 6,162,611 A | 12/2000 | Heller et al. |
| 6,163,714 A | 12/2000 | Stanley et al. |
| 6,168,957 B1 | 1/2001 | Matzinger et al. |
| 6,275,717 B1 | 8/2001 | Gross et al. |
| 6,424,847 B1 | 7/2002 | Mastrototaro et al. |
| 6,514,718 B2 | 2/2003 | Heller et al. |
| 6,520,326 B2 | 2/2003 | Mcivor et al. |
| 6,521,446 B2 | 2/2003 | Hellinga |
| 6,528,809 B1 | 3/2003 | Thomas |

(Continued)

OTHER PUBLICATIONS

Enson et al. In vivo studies with an intravascular and intracardiac reflection oximeter. J Appl Physiol, (17):552-558, 1962.

(Continued)

*Primary Examiner* — Christopher L Chin
(74) *Attorney, Agent, or Firm* — Dickinson Wright, PLLC (57) ABSTRACT

A system and method are provided for utilizing radiometric fluorescence detection to determine a glucose independent concentration value when measuring frequency bands that do not contain the system isosbestic point. Preferably two bands are chosen such that a first band is below the system isosbestic point, and a second band is above the system isosbestic point, and both points are sufficiently far from the frequency endpoints to maximize the signal to noise ratio.

9 Claims, 9 Drawing Sheets
(7 of 9 Drawing Sheet(s) Filed in Color)

(56) References Cited

U.S. PATENT DOCUMENTS

| | | |
|---|---|---|
| 6,546,269 B1 | 4/2003 | Kumik |
| 6,551,494 B1 | 4/2003 | Heller et al. |
| 6,560,471 B1 | 5/2003 | Heller et al. |
| 6,565,509 B1 | 5/2003 | Say et al. |
| 6,579,690 B1 | 6/2003 | Bonnecaze et al. |
| 6,585,707 B2 | 7/2003 | Cabiri et al. |
| 6,615,151 B1 | 9/2003 | Scecina et al. |
| 6,653,091 B1 | 11/2003 | Dunn et al. |
| 6,766,183 B2 | 7/2004 | Walsh et al. |
| 6,780,645 B2 | 8/2004 | Hayter et al. |
| 6,855,556 B2 | 2/2005 | Amiss et al. |
| 7,003,341 B2 | 2/2006 | Say et al. |
| 7,064,103 B2 | 6/2006 | Pitner et al. |
| 7,190,988 B2 | 3/2007 | Say et al. |
| 7,316,909 B2 | 1/2008 | Pitner et al. |
| 7,326,538 B2 | 2/2008 | Pitner et al. |
| 7,496,392 B2 | 2/2009 | Alarcon et al. |
| 7,629,172 B2 | 12/2009 | Alarcon et al. |
| 7,749,729 B2 | 7/2010 | Heinecke et al. |
| 7,851,593 B2 | 12/2010 | Hsieh et al. |
| 8,465,981 B2 | 6/2013 | Daunert et al. |
| 8,467,843 B2 | 6/2013 | Markle et al. |
| 8,470,300 B2 | 6/2013 | Clark et al. |
| 8,509,867 B2 | 8/2013 | Workman et al. |
| 2003/0153821 A1 | 8/2003 | Berner et al. |
| 2003/0211454 A1 | 11/2003 | Thomas et al. |
| 2004/0118681 A1 | 6/2004 | Hellinga et al. |
| 2005/0118726 A1 | 6/2005 | Schultz et al. |
| 2005/0239155 A1* | 10/2005 | Alarcon ............ G01N 33/54373 435/14 |
| 2007/0020181 A1 | 1/2007 | Workman et al. |
| 2007/0281368 A1 | 12/2007 | Hsieh et al. |
| 2008/0261250 A1 | 10/2008 | Heinecke et al. |
| 2008/0275318 A1 | 11/2008 | Lastovich et al. |
| 2008/0311675 A1 | 12/2008 | Thomas et al. |
| 2009/0104714 A1 | 4/2009 | Thomas et al. |
| 2010/0221188 A1 | 9/2010 | Clark et al. |
| 2011/0091919 A1 | 4/2011 | Ye et al. |
| 2011/0105866 A1 | 5/2011 | Markle et al. |
| 2011/0184259 A1 | 7/2011 | Alarcon et al. |
| 2011/0262363 A1 | 10/2011 | Srivastava et al. |
| 2012/0232251 A1 | 9/2012 | Pickup et al. |
| 2013/0060105 A1 | 3/2013 | Shah et al. |
| 2013/0060106 A1 | 3/2013 | Aasmul et al. |

OTHER PUBLICATIONS

Grant et al. A sol-gel based fiber optic sensor for local blood ph measurements. Sensors and Actuators, B(45):35-42, 1997.

Koronczi et al. Development of a submicron optochemical potassium sensor with enhanced stability due to internal reference. Sensors and Actuators, B(51):188-195, 1998.

De Lorimier et al. Construction of a fluorescent biosensor family. Protein Science, (11):2655-2675, 2002.

Malchoff et al. A Novel Noninvasive Blood Glucose Monitor. Diabetes Care 25:2268-2275, 2002.

Weidemaier et al. Multi-day pre-clinical demonstration of glucose/galactose binding protein-based fiber optic sensor. Biosensors and Bioelectronics, (26):4117-4123, 2011.

Khan et al. Fluorescence intensity- and lifetime-based glucose sensing using glucose/galactose-binding protein. J Diabetes Sci Technol, 7(1):62-71, Jan. 2013.

Khan et al. Fluorescence intensity- and lifetime-based glucose sensing using an engineered high-Kd mutant of glucose/galactose-binding protein. Analytical Biochemistry 399 (2010) 39-43.

Pickup et al. Fluorescence intensity- and lifetime-based glucose sensing using glucose/galactose-binding protein. J Diabetes Sci Technol, 7(1):62-71, Jan. 2013.

* cited by examiner

SYSTEM AND METHOD FOR DIAGNOSING SENSOR PERFORMANCE USING ANALYTE-INDEPENDENT RATIOMETRIC SIGNALS

This application claims the benefit under 35 U.S.C. § 119(e) of U.S. Provisional Application No. 61/728,488, filed Nov. 20, 2012, in the U.S. Patent and Trademark Office, the entire disclosure of which is hereby incorporated by reference.

BACKGROUND OF THE INVENTION

1. Field of the Invention

The present invention relates to a system and method for diagnosis of sensor performance. More particularly, the present invention relates to a system and method for diagnosing sensor performance using analyte-independent ratiometric signals.

2. Description of the Related Art

Glucose sensors are an essential element in diabetes management. In particular, continuous glucose sensors provide numerous advantages over episodic glucose sensors or conventional finger-stick glucose test strips. Critical to the success of a continuous glucose sensor, however, is a determination or diagnosis of the performance of the sensor. Existing continuous glucose sensors become less sensitive over time, and eventually fail and need to be replaced. As such, it is important to monitor the performance of a continuous glucose sensor, and to replace the sensor when the performance drops below an acceptable level.

One difficulty with fluorescence measuring systems is due to the inherently noisy nature of intensity signals. Ratiometric sensing takes advantage of a very stable property of dye emission spectra. That is, the ratio of different bands within the spectra is relatively insensitive to changes in the overall intensity of the spectra. Fluctuations in emission power or optical efficiency of the system, within limits, do not affect the measured ratio between different frequency bands, provided that the chosen bands are reasonably noise-free. Continuous glucose sensors based on a fluorescently-labeled glucose binding protein (GBP) can take advantage of ratiometric sensing to obtain more accurate readings.

Figure 1:
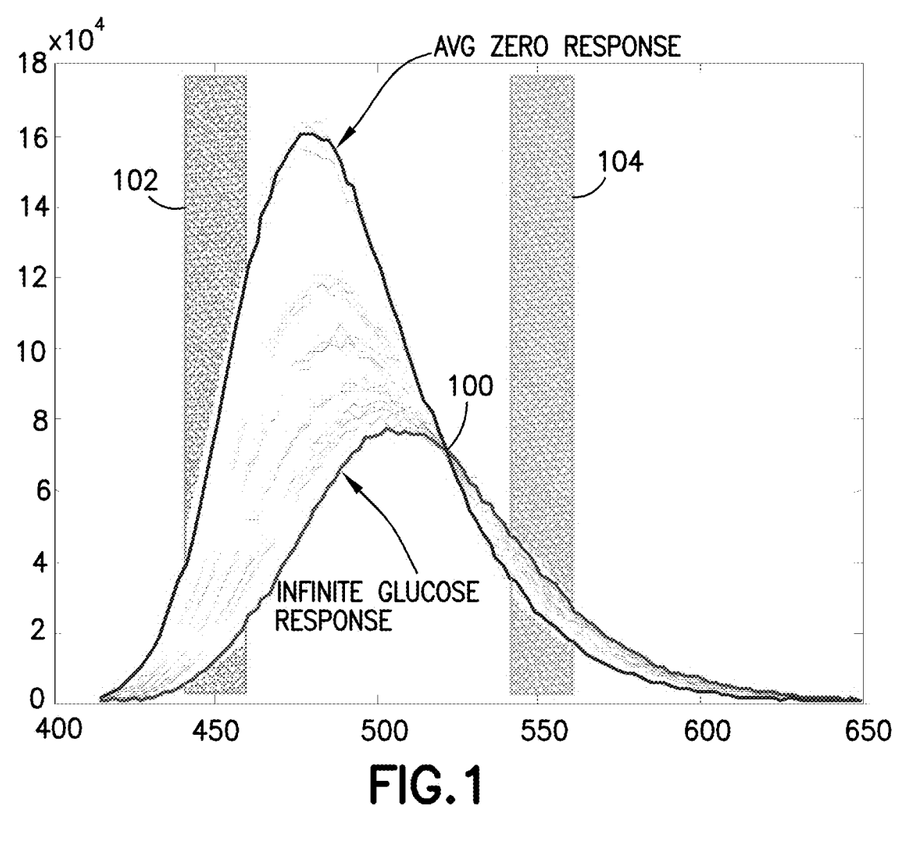
FIG. 1 is an illustration of spectral bands of an exemplary acrylodan dye-labeled GBP in a range of glucose concentrations.

As shown, for example, in FIG. 1, the frequency response for a labeled GBP-based continuous glucose sensor includes an isosbestic point 100. That is, there is a frequency for which intensity response is independent of the concentration of the target analyte. The isosbestic point has been used to measure sensor performance independent of analyte concentration. The isosbestic point signal, however, has no utility in the measurement of the analyte concentration, since by its nature it does not change in response to analyte concentration. In existing ratiometric systems, different frequency bands must be measured to determine glucose concentration since the intensity at the isosbestic point does not correlate to glucose concentration. When neither of the measured frequency bands is narrowly centered on the isosbestic point of the spectra, diagnosing intensity disturbances is more difficult because both measured intensity bands change in response to both analyte concentration changes and system changes. It would be beneficial to be able to extract a noise free signal which corresponds to analyte concentration only and an analyte independent signal which corresponds to system status only, without requiring measurement of the isosbestic point in addition to at least two other frequencies. Such a combination has not been previously demonstrated with a continuous GBP detection system.

Accordingly, there is a need for a system and method for diagnosing sensor performance using analyte independent ratiometric signals. In such a system, preferably the same signals may be used for both analyte measurement and analyte-independent diagnosis, thereby minimizing system complexity and the number of measurements that must be taken. A signal pair is preferably selected to optimize the best possible analytical signal, such as for the highest signal to noise ratio over the expected analytical range, while still providing a sensor diagnostic capability.

SUMMARY OF THE INVENTION

According to one aspect of embodiments of the present invention, a method of performing a diagnostic test on an analyte sensor is provided. The method includes introducing matrix suspended glucose binding protein (GBP) labeled with an environmentally sensitive dye to an analyte environment. The dye fluoresces at an intensity related to a concentration of the analyte concentration in the environment. A first fluorescent intensity is measured at a first frequency component that is higher than an isosbestic frequency of the dye. A second fluorescent intensity is measured at a second frequency component that is lower than the isosbestic frequency. A glucose independent intensity coefficient (GIIC) value is determined based on the first and second fluorescent intensities. Finally, a performance of the analyte sensor is determined based on the GIIC value.

According to another aspect of embodiments of the present invention, a system for performing a diagnostic test on an analyte sensor is provided. The system comprises a matrix suspended, fluorescent dye-labeled glucose binding protein (GBP) element adapted for introduction to an analyte environment. The system further includes a fluorescence intensity measuring device for measuring fluorescence intensity at first and second respective frequencies, the first frequency being higher than an isosbestic frequency of the dye, and the second frequency being lower than the isosbestic frequency. The system includes a processor for determining a glucose independent intensity coefficient (GIIC) value based on the first and second measured fluorescence intensities, and for determining a performance of the analyte sensor based on the determined GIIC value. Finally, the system includes an output device for providing an output indicative of the determined performance.

BRIEF DESCRIPTION OF THE DRAWING FIGURES

The patent or application file contains at least one drawing executed in color. Copies of this patent or patent application publication with color drawing(s) will be provided by the Office upon request and payment of the necessary fee.

These and other features and advantages of the present invention will become more apparent from the detailed description of exemplary embodiments with reference to the attached drawings in which.

Throughout the drawings, like reference numerals will be understood to refer to like features and structures.

DETAILED DESCRIPTION OF EXEMPLARY EMBODIMENTS

As will be described in further detail below, it has been discovered that an analyte independent signal can be derived from measurements taken at frequencies away from the isosbestic frequency. That is, the same two analyte correlated measurements used for ratiometric determination of analyte concentration can also advantageously be used to derive and measure an analyte independent sensor performance which can be used to perform diagnostics on the sensor. In any ratiometric fluorescence detection system (such as the BD GBP glucose sensor), where spectral ratios change in response to analyte concentration, even if the intensity bands do not contain the system isosbestic point, an intensity value which is insensitive to analyte concentration can be calculated. This glucose independent concentration has diagnostic potential that intensity bands individually do not.

For any two bands within the emission spectrum of a fluorescent dye such as acrylodan, a ratio can be found which is a function of glucose concentration:

$$R = \{R0 + Rinf([G]/KD)\}/(1+[G]/KD) \quad (1)$$

where
[G]=glucose concentration
R=ratio at given glucose concentration
R0=ratio of spectral bands at zero glucose concentration
Rinf=ratio of spectral bands at infinite (saturating) glucose concentration
KD=apparent dissociation constant for system
which can be rewritten as $$[G] = KD(R-R0)/(Rinf-R). \quad (2)$$

It is also true that this equation can be written for any spectral band (or for peak intensity, or spectral center of mass, among other properties). Specifically, this equation can be written for each spectral band used to construct the ratiometric signal.

$$[G] = KDb(Fb-Fb0)/(Fbinf-Fb), \quad (3)$$

and $$[G] = KDg(Fg-Fg0)/(Fginf-Fg), \quad (4)$$

where Fb and Fg are intensity measurements of the "blue" 102 and "green" 104 intensity components (see FIG. 1).

Equating equations (3) and (4) provides, $$KDb(Fb-Fb0)/(Fbinf-Fb) = KDg(Fg-Fg0)/(Fginf-Fg) \quad (5)$$

and rearranging to put the variable intensity terms on the left hand side of the equation results in:

$$(KDg/KDb-1)*Fb*Fg+Fb*(Fginf-(KDg/KDb)*Fg0)+Fg(Fb0-(KDg/KDb)*Fbinf)=Fb0*Fginf-(KDg/KDb)*Fg0*Fbinf \quad (6)$$

As can be appreciated, the right hand side of equation (6) contains only terms not dependent on glucose (glucose Independent Intensity, or GII). Accordingly, the left hand side of equation (6) must also be independent of glucose.

$$(KDg/KDb-1)*Fb*Fg+Fb*(Fginf-(KDg/KDb)*Fg0)+Fg(Fb0-(KDg/KDb)*Fbinf)=GII \quad (7)$$

Using the notation QF=Finf/F0, we arrive at:

$$(KDg/KDb-1)*Fb*Fg+Fb*Fg0*(QFg-KDg/KDb)+Fg*Fb0*(1-(KDg/KDb)*QFb)=GII \quad (8)$$

Letting
A=(KDg/KDb−1)
B=Fg0*(QFg−KDg/KDb)
C=Fb0*(1−(KDg/KDb)*QFb)
we arrive at:

$$A*Fb*Fg+B*Fb+C*Fg=GII \quad (9)$$

or $$A/C*Fb*Fg+B/C*Fb+Fg=GII/C \quad (10)$$

So we define $$w=B/C=(QFg-KDg/KDb)/(KDg/KDb-QFb)*Fg0/Fb0.$$

such that equation (10) becomes:

$$A/C\,Fb*Fg+wFb+Fg=GII/C \quad (11)$$

Equation (11) can be normalized as follows:

$$A/C/(1+w)*Fb*Fg+(wFb+Fg)/(1+w)=GII/C/(1+w) \quad (12)$$

For the case where KDg/KDb is close to 1, A becomes small so equation (11) reduces to:

$$(wFb+Fg)/(1+w)=GII/C/(1+w) \quad (13)$$

In equation (13), the variable "w" can be referred to as the glucose independent intensity coefficient (GIIC). In the case where KDg/KDb is close to 1, w can be approximated as $$w=(QFg-1)/(1-QFb)*Fg0/Fb0 \quad (14)$$

As discussed above, fluorescence-based sensors are notoriously sensitive to intensity variations due to changes in, for example, optical path efficiency and dye quantum yield. Signals which are not responsive to the analyte in question are often used to provide a reference to track some of these intensity variations, provided that the noise generating event impacts both signals in the same way. For this reason, ratiometric sensing is often used. A ratio of two components of the fluorescent output can be directly related to analyte concentration, and that ratio is explicitly not affected by overall changes in the fluorescent intensity. However, the ratiometric signal has not been considered to hold diagnostic information about the system, as changes in the analyte concentration could not previously be separated from the signal changes.

In embodiments of the present invention however, the same signal pair used to generate analyte concentration information can be used to generate diagnostic information. Further, no calculation of the analyte concentration is required in order to make the diagnostic determination.

A preferred embodiment for glucose sensing utilizes the same general design principles considered for existing glucose GBP sensors. For examples of GBP sensors, see international patent applications WO 2006/044973, published Apr. 27, 2006, WO 2007/124464, published Nov. 1, 2007, and WO 2008/131360, published Oct. 30, 2008, the entire contents of which are hereby incorporated by reference. Such sensors are preferably small size, long life sensors, with strong signal to noise characteristics, and low power consumption. Use of the signals to provide diagnostic information advantageously does not change the overall physical characteristics of the sensor system. The additional calculations required to derive the analyte independent signal may be performed within the same computing architecture used to process the raw sensor signal and calculate analyte concentration.

An exemplary embodiment of the invention is targeted to the glucose binding protein (GBP) continuous glucose sensor. This sensor uses a specific protein-dye combination to generate a fluorescent signal, and measures the output in two specific wavelength bands. One wavelength band is preferably a frequency higher than the isosbestic point, and the other wavelength is preferably a frequency lower than the isosbestic point. Preferably, the high and low frequency bands are selected to balance maximum separation from the isosbestic frequency with maximum signal to noise ratio within the relevant expected analyte concentration range. Accordingly, the high and low frequencies are selected to be far from the isosbestic frequency, without being too far, since the analyte correlated signal decreases at extreme ends of the spectrum.

As will be appreciated, variations in the protein-dye combinations can be made while maintaining the general ratiometric output, and these binding proteins can be targeted to analytes other than glucose. See, for example, R. M. de Lorimier, J. J. Smith, et al., *Construction of a Fluorescent Biosensor Family*, Protein Sci 11 (11) 2655-2675 (2002), for a list of binding proteins and dye combinations.

This method can be applied to Förster Resonant Energy Transfer (FRET)-based systems as well. In this case, the two signal parts originate from two different dyes located in close proximity.

The fluorescent signal generated by the dye in, for example, a GBP glucose sensor is a spectrum covering a range of wavelengths. The signal at each wavelength is affected by the same phenomena. That is, analyte concentration and dye concentration. In a ratiometric sensing system, although the source of intensity changes throughout the spectrum is the same, the impact on various parts of the emission spectrum are different. These changes can be characterized for the entire spectrum in a stable environment, such as during factory calibration of a sensor. The mathematical relationships which describe the impact of the analyte can therefore be determined for all parts of the spectrum. In a ratiometric sensing system according to an embodiment of the invention, the pair of relationships describing the fluorescence signals can advantageously be combined to yield both a measurement of the analyte concentration and a measurement of average signal strength which does not change with the analyte concentration.

Example 1: Solution Spectra (GBP-Acrylodan)

Figure 2:
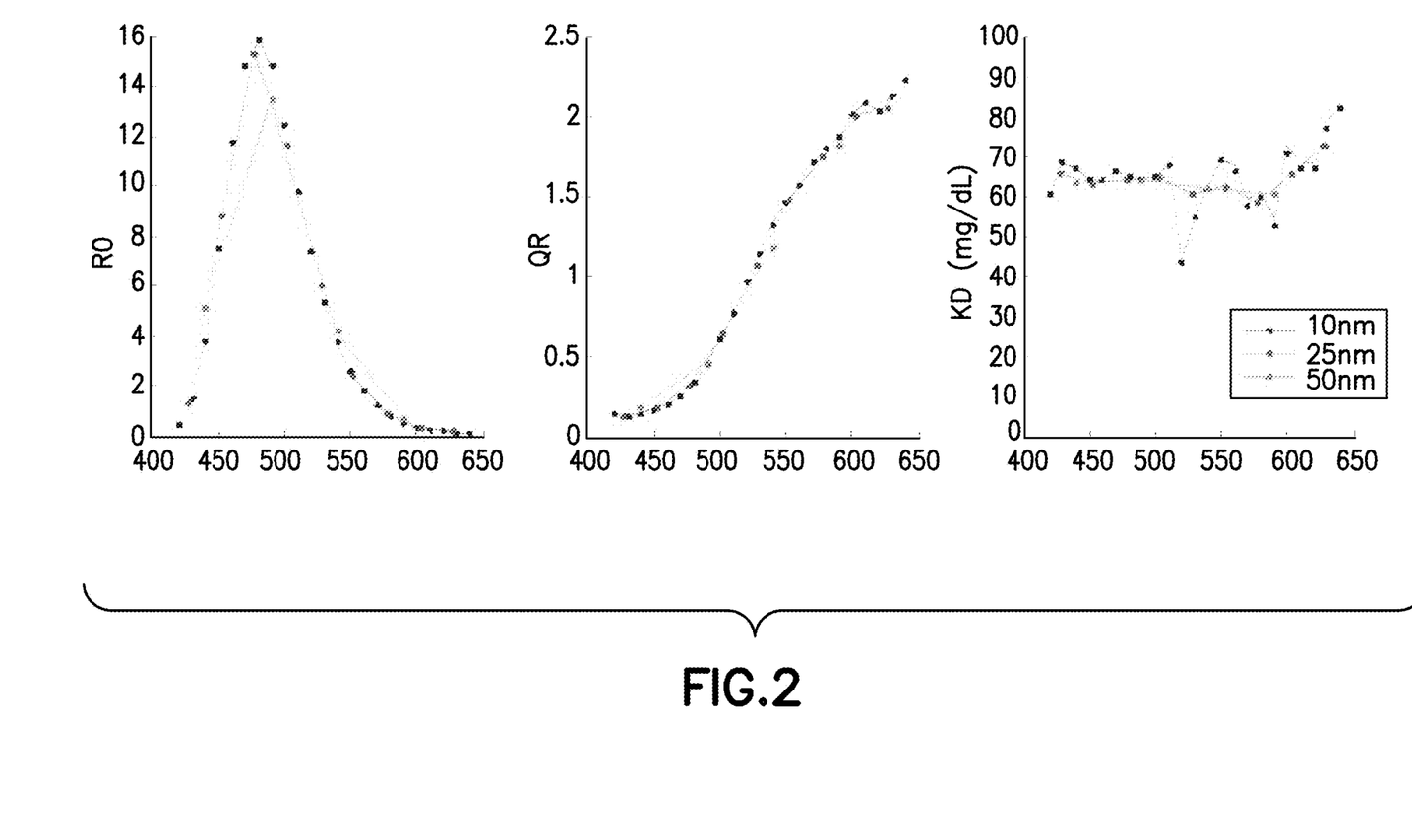
FIG. 2 is an illustration of various calibration parameters for acrylodan/GBP spectra.
Figure 3:
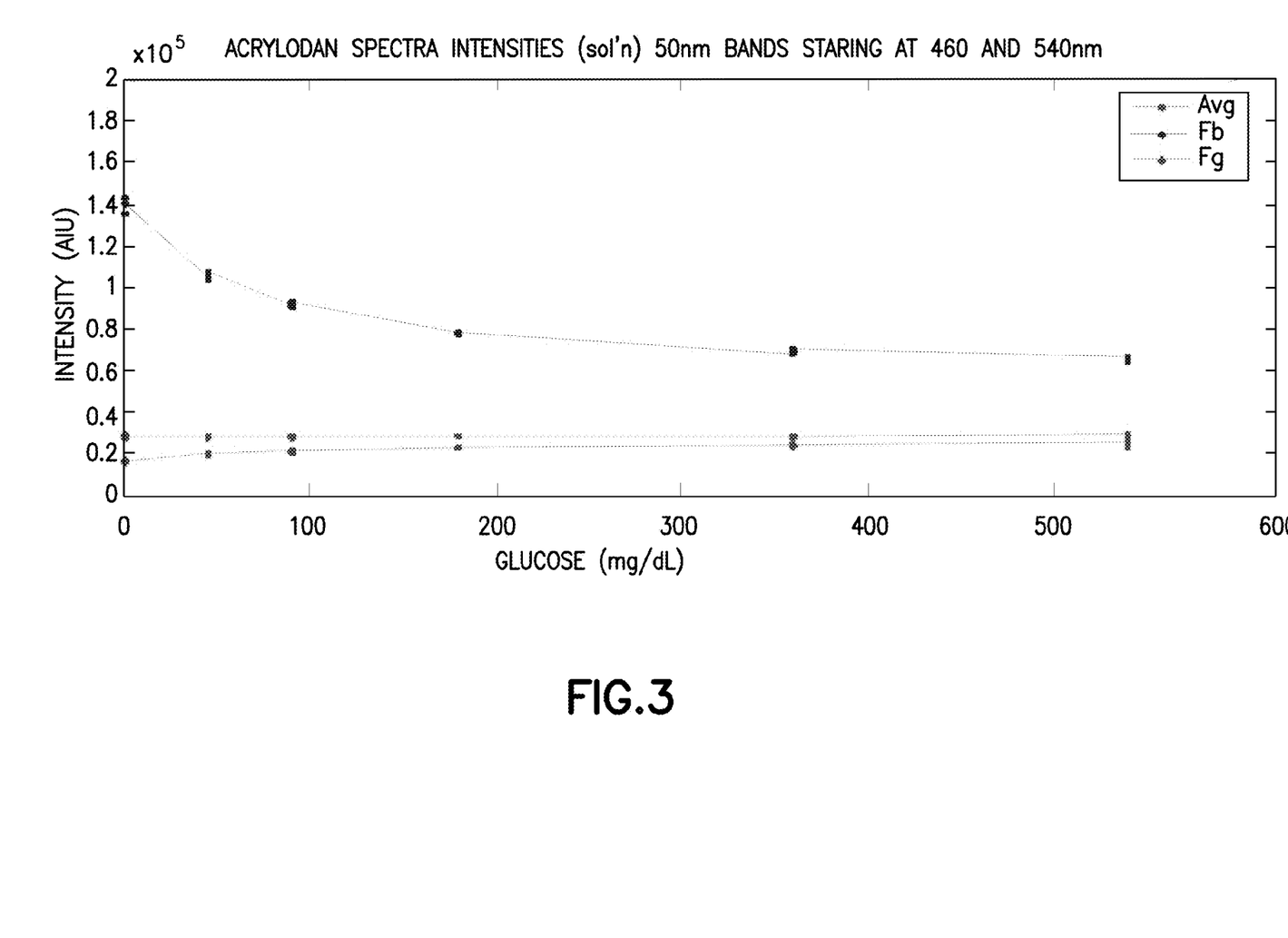
FIG. 3 is an illustration of exemplary acrylodan/GBP spectral bands in solution.

Spectra from GBP-acrylodan in solution were taken (triplicate measurements at 0, 2.5, 5. 10, 20, 30 mM, FP001 Vial 1 Titration Curve 061008, FIG. 1). Spectra from solutions of PBS buffer without protein, dye or glucose (background) were subtracted from all curves. Calibration curves were determined at each wavelength in order to calculate an infinite glucose response curve and to determine how calibration parameters changed as a function of wavelength (FIG. 2). R0 is precisely the mean zero-response curve. Qx (response at infinite glucose/response at zero) varied according to a 4-parameter logistic curve across the wavelength region examined. As expected, the point where Q=1 is 523 nm, close to the visually observed isosbestic point. KD is approximately constant across the spectrum, although there is considerably more variability when wavelengths are greater than the isosbestic point, due most likely to small dynamic range and thus small signal to noise ratio. For a set of reasonable wavelength window sizes, the KDs are not significantly different on either side of 523 nm (p>0.1, Student's t test). Considering a single pair of wavelength bands centered at 460 and 560 nm, an average intensity according to equation (12) was calculated (FIG. 3). Note that the glucose independent intensity is stable whereas the blue and green band intensities vary considerably across the glucose range. For this solution based data, the correction factor GIIC=0.12, and KDg/KDb=0.96.

For maximum dynamic range, a ratio derived from bands separated as widely as possible will provide the largest range (i.e. QR=QFg/QFb, and maximum QFg and minimum QFb are obtained near edges of spectrum, see center plot in FIG. 2). However, from an overall system performance viewpoint, the dynamic range must be balanced against the loss of signal to noise ratio as intensities drop near the edges of the spectrum. From a diagnostic point of view, a wavelength band centered at the isosbestic point could provide diagnostic information but not analyte concentration information. The use of two wavelength bands to generate an analyte-independent intensity allows wavelength band choice to be driven by system performance objectives, while still providing a diagnostic capability.

Example 2: Lab Setup (25ga SensorGBP-Acrylodan)

Figure 4:
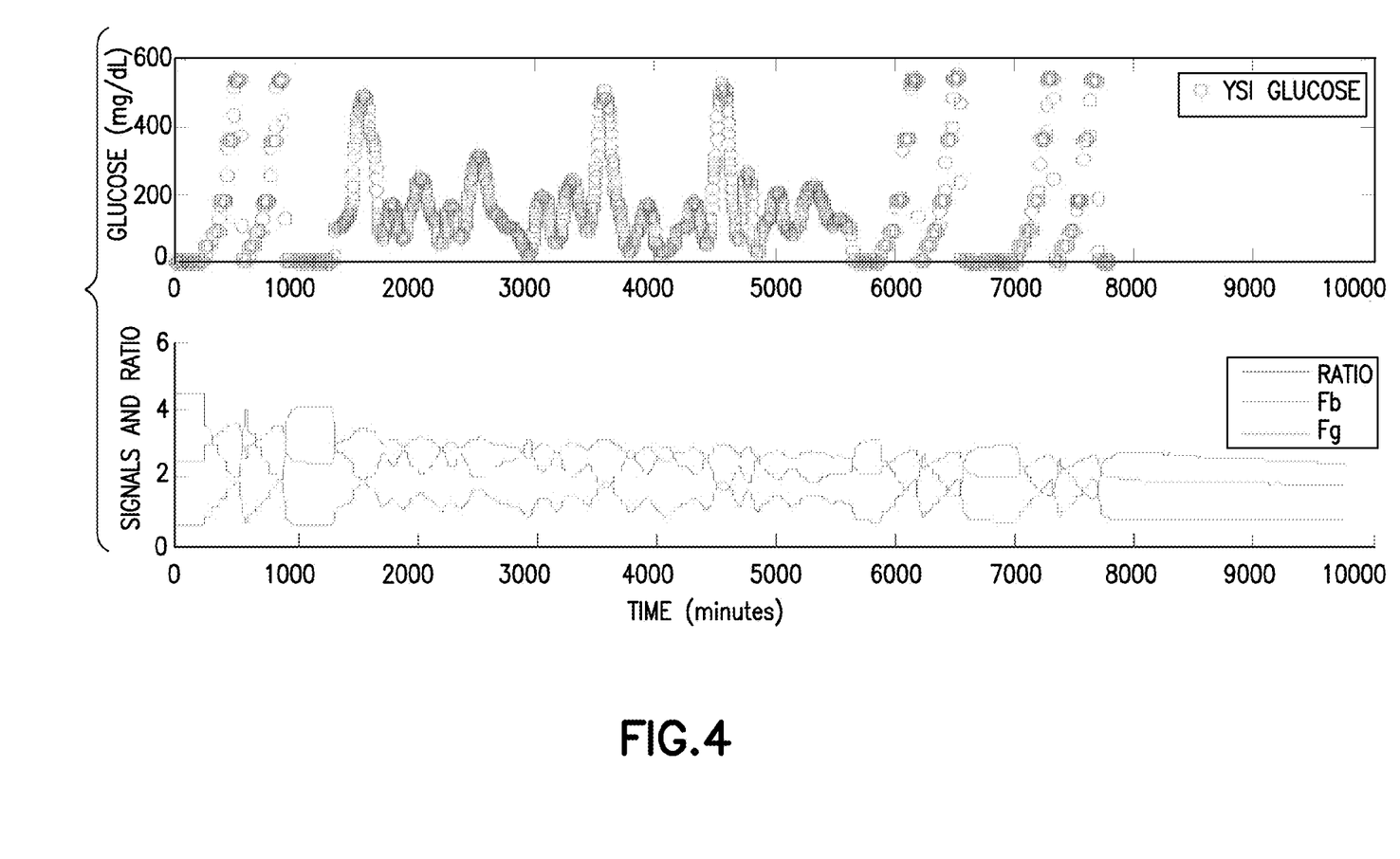
FIG. 4 illustrates exemplary actual glucose against green and blue band measurements using an acrylodan/GBP sensor according to an embodiment of the present invention.
Figure 5:
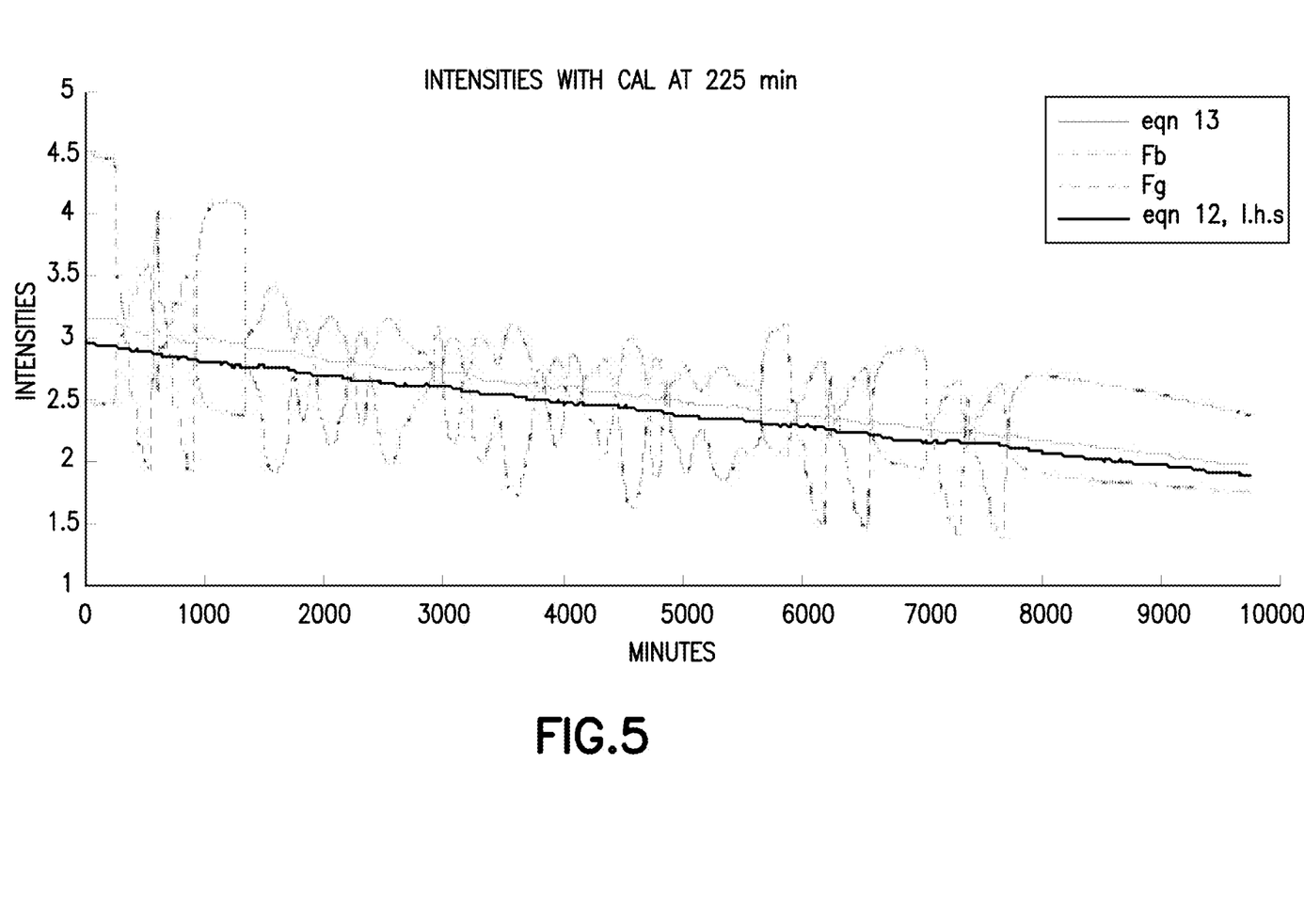
FIG. 5 illustrates glucose independent intensity values derived from blue and green band measurements according to an exemplary embodiment of the present invention.

Sensor intensities from a 3 day lab experiment were analyzed. PEG/GBP-acrylodan sensors were exposed to a continuously variable glucose profile at 34° C. for 3 days. The profile included two calibration ladders before and after three days of variable glucose (FIG. 4). The first calibration ladder was used to calculate calibration parameters for each wavelength band. Glucose independent intensity according to equation (12) was calculated. Intensity decay due to photobleaching during the calibration ladders causes a misestimation of calibration parameters. To correct this, an intensity decay model [I=aN+b+c*exp(−N/tau), N=exposure number] was used to adjust the measured intensities. Binding equation calibration parameters were recalculated for the first ladder, and a glucose independent intensity was calculated, as shown in the solid lines in FIG. 5. As can be observed in FIG. 5, although minor fluctuations remain, the resulting intensity curve is very stable in the face of large glucose concentration excursions. The solution of equation (13) (intensity product term is dropped) yields a similar curve (blue solid line in FIG. 5), but with slight intensity variations during the first two calibration ladders. As a measure of variability, coefficient of variation (std/mean) was computed for each curve. Blue and green intensities had a CV of 29 and 14% respectively, even after correction for long term photobleaching decay. In contrast, the glucose independent intensity had a CV of <1%, again accounting for long term photobleaching. For this sensor, the correction factor GIIC=0.516, and KDg/KDb=0.91.

As will be appreciated, the glucose independent intensity also provides a very smooth signal from which long term effects like photobleaching can be assessed.

Example 3: Feasibility Trial (31 Ga SensorGBP-Acrylodan

Figure 6:
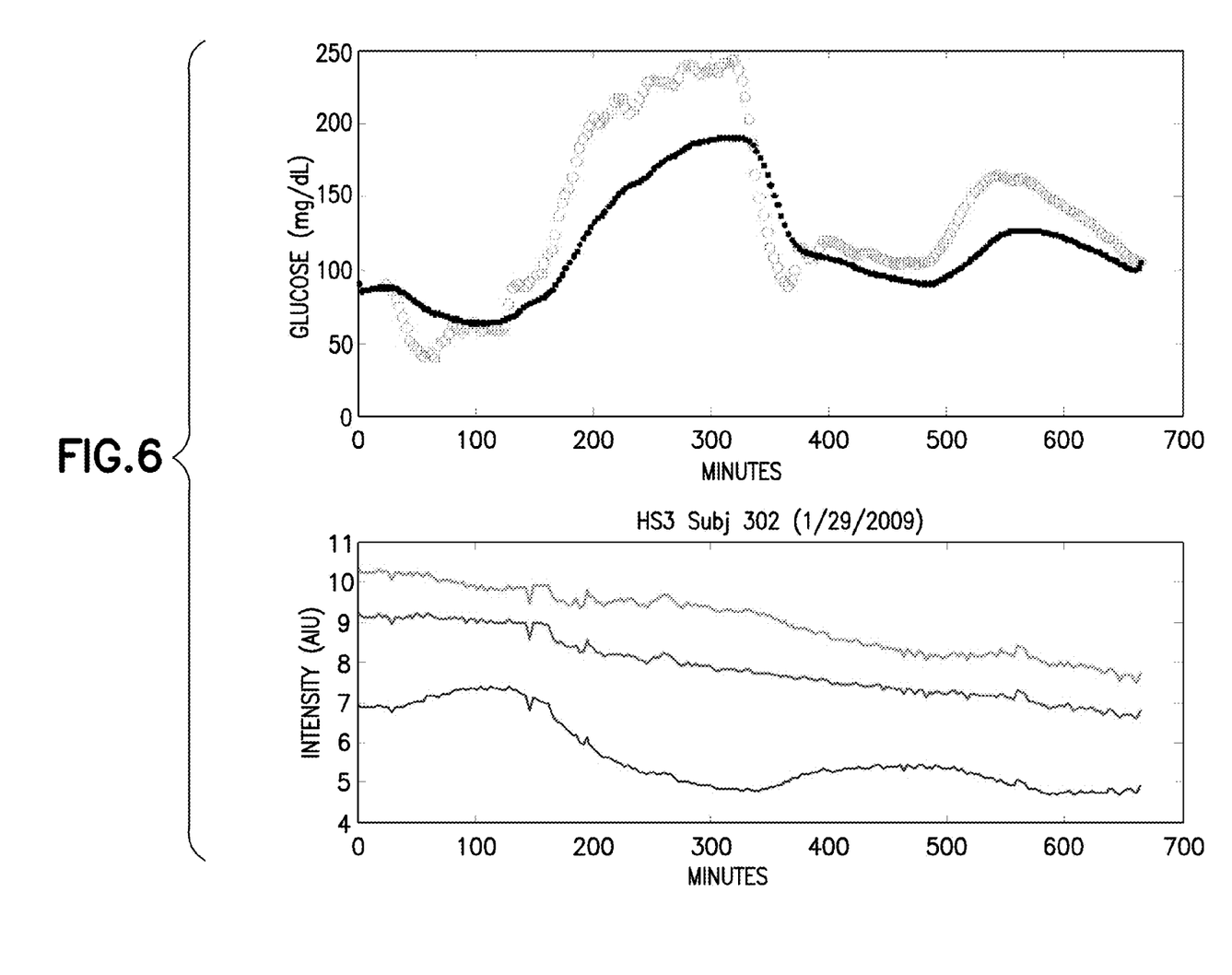
FIG. 6 illustrates actual and sensor-calculated glucose measurements over time, as well as blue and green band measurements and a glucose-independent intensity derived from the blue and green bands in a properly functioning continuous acrylodan/GBP sensor according to an exemplary embodiment of the present invention.
Figure 7:
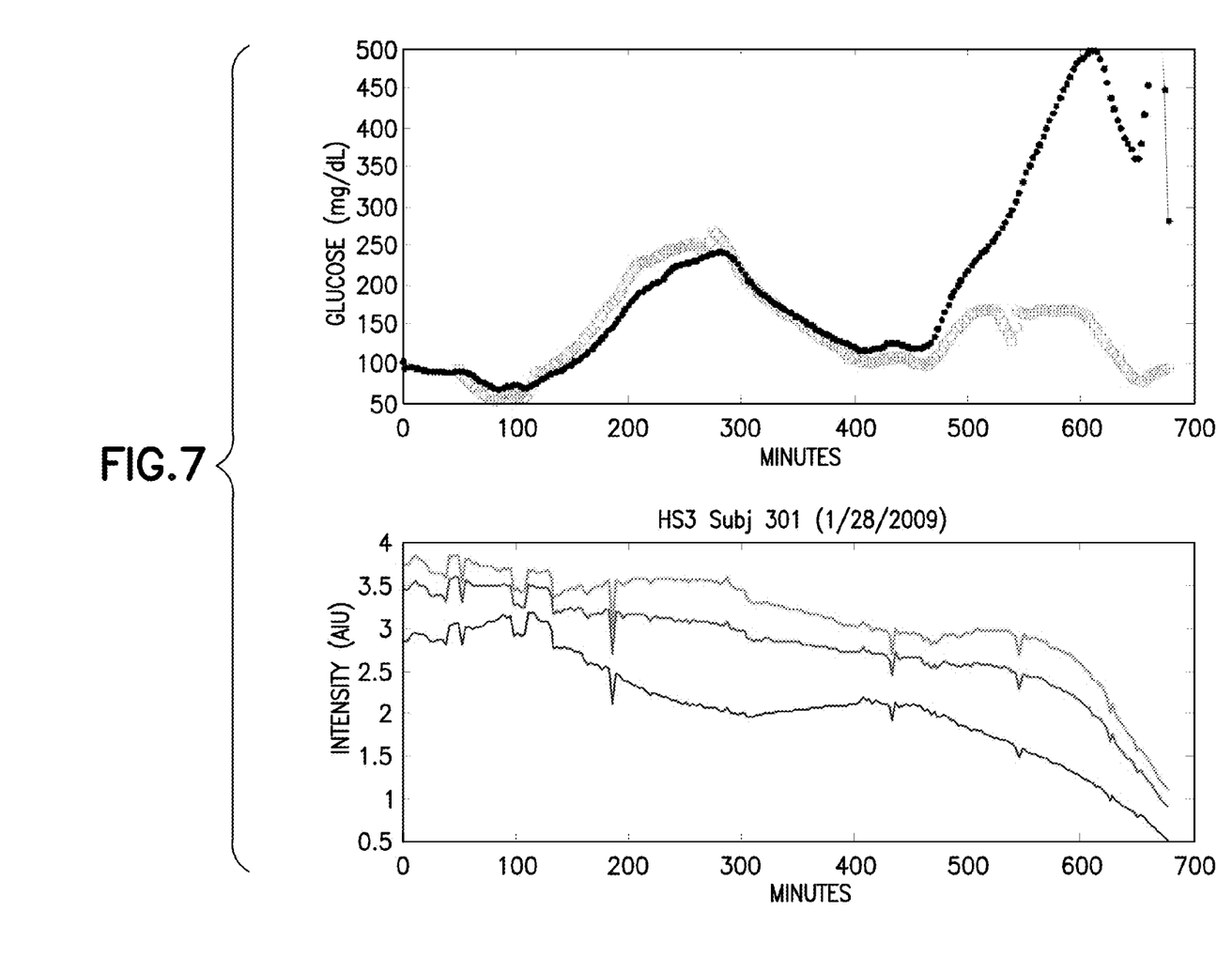
FIG. 7 illustrates actual and sensor-calculated glucose measurements over time, as well as blue and green band measurements and a glucose-independent intensity derived from the blue and green bands in a malfunctioning continuous acrylodan/GBP sensor according to an exemplary embodiment of the present invention.

For this example the output from two 31 ga butterfly sensors was used, placed in ID and SC tissue during a feasibility trial. Due to poor KD estimates from 3-point calibrations, GIIC values of 0.5 were assumed. Intensities were normalized by the optical standard in use during this trial before calculations were performed. The first sensor (302 A-ID, FIG. 6) intensity decay is stable throughout the test. Note that although glucose estimates have a small dynamic range relative to true values, the sensor estimates are stable. The second sensor (301 B-SC, FIG. 7) intensity decay accelerates markedly after 550 minutes, and follows a marked overestimation of glucose. Due to glucose excursion, blue and green intensities are moving in opposite directions at 500 minutes. As can be appreciated, glucose independent intensity advantageously allows detection of accelerated decay even when glucose is changing.

As can be seen, the use of intensity ratios from fluorescence signatures provides a robust analyte measurement system. Using the same intensity information, an analyte independent signal can be derived, which allows separation of sensor output changes into those caused by analyte change and those caused by other factors. The generation of a glucose independent intensity has been demonstrated for in vitro and in vivo applications of a GBP glucose sensor.

Figure 8:
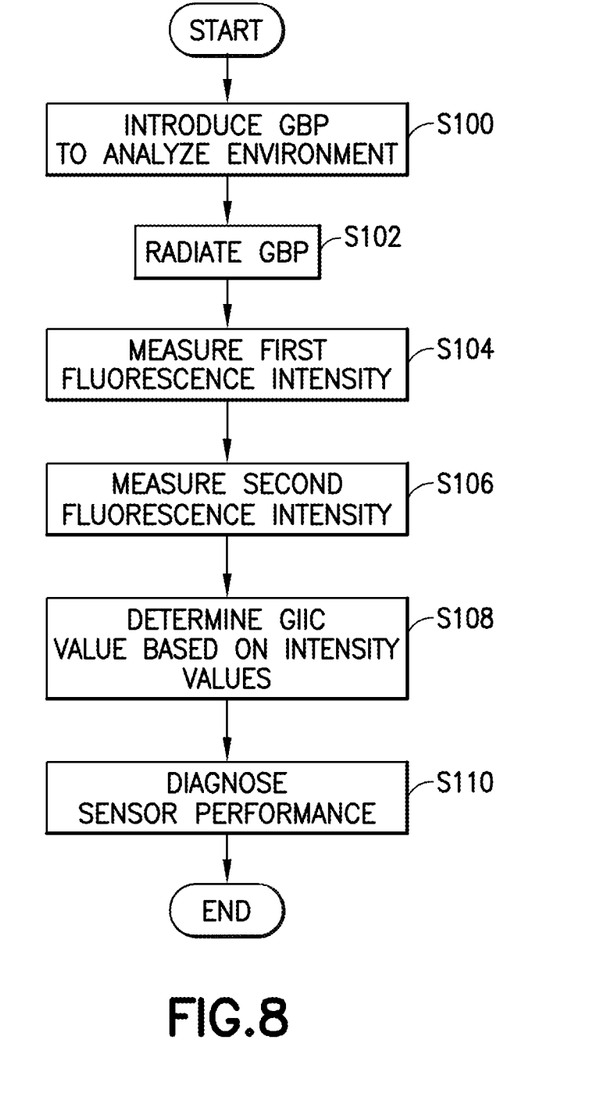
FIG. 8 illustrates an exemplary method of determining sensor performance according to an embodiment of the invention.

An exemplary method according to an embodiment of the invention will not be described in connection with FIG. 8. A matrix suspended analyte binding protein, such as a glucose binding protein (GBP) is introduced to the analyte environment at step S100. The binding protein is labeled with a dye that fluoresces with an intensity spectrum related to a concentration of the analyte concentration in the environment. A source of electromagnetic radiation is directed to the GBP at step S102, and the radiation causes the GBP to fluoresce. At step S104, a first fluorescence intensity is measured at a first frequency component. The first frequency component is preferably higher than the isosbestic frequency of the dye (green range). At step S106, a second fluorescence intensity is measured at a second frequency component. The second frequency component is preferably lower than the isosbestic frequency of the dye (blue rance). At step S108, a GIIC value is determined based on the measured first and second fluorescence intensities. At step S110, sensor performance is diagnosed based on the determined GGIC value.

Figure 9:
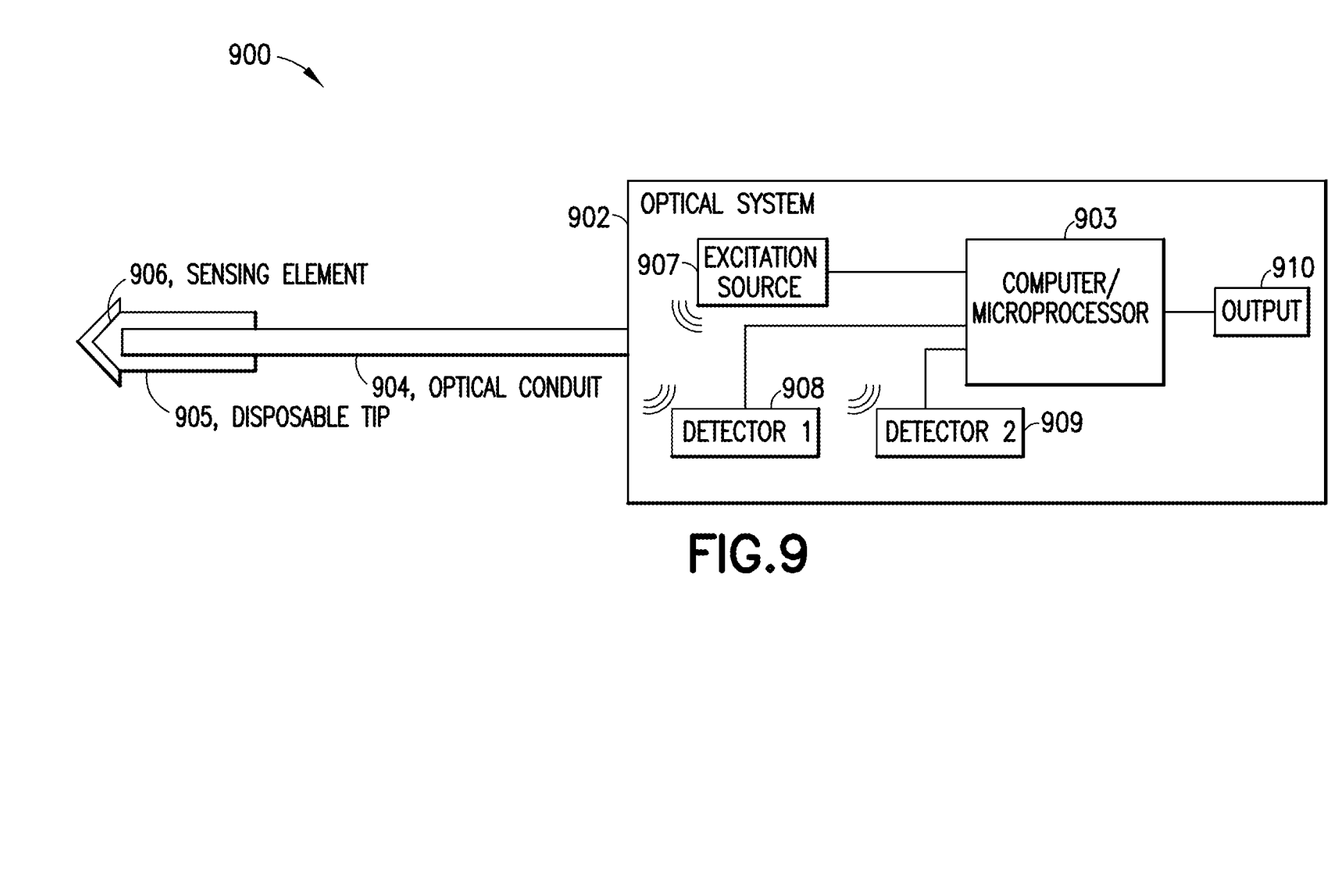
FIG. 9 illustrates an exemplary device according to an embodiment of the present invention.

An exemplary system according to an embodiment of the present invention will now be described in connection with FIG. 9. The system 900 includes a main body 902 that includes an optical system and a computer, microprocessor or any other suitable processor 903. An optical conduit 904 such as an optical fiber connects the main body 902 to a sensing tip 905. The sensing tip 905 includes a sensing element 906 such as matrix suspended GBP. The matrix suspended GBP is preferably small, and may be introduced to an analyte environment, such as subcutaneous or intradermal tissue via a rigid or semi-rigid conduit such as a needle or cannula.

The optical system preferably includes an excitation source 907 to generate light which is directed into the optical conduit 904 and into the sensing element 906. The optical system further preferably includes first and second detectors 908, 909 to detect the intensity of fluorescence signals received from the sensing element 906 via the optical conduit 904. The first detector 908 preferably detects fluorescence intensity at a first frequency that is higher than the isosbestic point of the dye with which the GBP is labeled. The second detector 909 preferably detects fluorescence intensity at a second frequency that is lower than the isosbestic point of the dye. The processor 903 preferably controls operation of the system, including powering the excitation source. The processor 903 also receives the detected intensity measurements from detectors 908, 909, and determines a GIIC value based on the measured intensities. The processor further determines a performance of the sensor based on the determined GIIC value. The processor is further connected to an output device 910, and can control the output device 910 to provide an output indicative of the determined performance. As an example, the output device 910 may provide an audible alert of the processor 903 determines that the sensor performance has declined beyond a predetermined threshold.

While the invention has been shown and described with reference to certain embodiments thereof, it will be understood by those skilled in the art that various changes in form and details may be made therein without departing from the spirit and scope of the invention as defined by the appended claims.

What is claimed is:

1. A system for performing a diagnostic test on an analyte sensor, comprising:
a sensing element comprising a polyethylene glycol matrix suspended analyte binding protein element introduced to an analyte environment, said binding protein labeled with a dye fluorescing with an intensity spectrum related to a concentration of said analyte concentration in said environment; the sensing element disposed at a distal end of an optical conduit;
an excitation source at a proximal end of the optical conduit for supplying excitation energy to the optical conduit and a fluorescence intensity measuring device comprising first and second detectors for measuring fluorescence intensity at first and second respective frequencies, the first frequency being higher than an isosbestic frequency of the dye, and the second frequency being lower than the isosbestic frequency of the dye;
a microprocessor that stores and executes program instructions to determine a GIIC value based on the first and second measured fluorescence intensities, and to determine a performance of the analyte sensor based on the determined GIIC value; and
an output device electrically connected to the microprocessor that receives the GIIC value from the microprocessor and provides an output indicative of the determined performance;
wherein said microprocessor executes program instructions to calculate a glucose independent intensity according to the following equation:

$$GII=(KDg/KDb-1)*Fb*Fg+Fb*(Fginf-(KDg/KDb)*Fg0)+Fg(Fb0-(KDg/KDb)*Fbinf)$$

where

GII is the glucose independent intensity;

Fb is the measured intensity of the first frequency component;

Fg is the measured intensity of the second frequency component;

KDg is the apparent dissociation constant determined when using only the second frequency component;

KDb is the apparent dissociation constant determined when using only the first frequency component;

Fginf is the intensity of the second frequency component at saturated concentration;

Fg0 is the intensity of the second frequency component at zero concentration;

Fbinf is the intensity of the first frequency component at saturated concentration; and Fb0 is the intensity of the first frequency component at zero concentration.

2. The system of claim 1, wherein the analyte binding protein is a glucose binding protein.

3. The system of claim 1, wherein said analyte is glucose.

4. The system of claim 1, wherein said microprocessor calculates a ratio between the first frequency component and the second frequency component for the dye is defined by:

$$R=(R0+R\text{inf}([G]/KD))/(1+[G]/KD)$$

where

[G] is the analyte concentration;

R is the ratio at a given analyte concentration;

R0 is the ratio of spectral bands at zero analyte concentration;

Rinf is the ratio of spectral bands at infinite (saturating) analyte concentration; and KD is an apparent dissociation constant for the system.

5. The system of claim 4, wherein the analyte is glucose, and [G] is the glucose concentration.

6. The system of claim 1, wherein the microprocessor processes raw sensor signals and also calculates analyte concentration.

7. The system of claim 1, wherein the first frequency and the second frequency are selected to be frequencies at which the signal to noise ratio is greater than 90% of the maximum signal to noise ratio.

8. The system of claim 1, wherein the first fluorescent intensity is generated by a first dye and the second fluorescent intensity is generated by a second dye.

9. A system for performing a diagnostic test on a glucose sensor, comprising:

a sensing element comprising a polyethylene glycol suspended glucose binding protein element suspended within a matrix for introduction to a glucose environment, said binding protein labeled with a dye fluorescing with an intensity spectrum related to a concentration of said analyte concentration in said environment; the sensing element disposed at a distal end of an optical conduit;

an excitation source at a proximal end of the optical conduit for supplying excitation energy to the optical conduit and a fluorescence intensity measuring device comprising first and second detectors for measuring fluorescence intensity at first and second respective frequencies, the first frequency being higher than an isosbestic frequency of the dye, and the second frequency being lower than the isosbestic frequency of the dye;

a microprocessor that stores and executes program instructions to determine a GIIC value based on the first and second measured fluorescence intensities, and for determining a performance of the glucose sensor based on the determined GIIC value; and an output device device electrically connected to the microprocessor that receives the GIIC value from the processor and to provide an output indicative of the determined performance;

wherein said microprocessor executes program instructions to calculate a glucose independent intensity according to the following equation:

$$GII=(KDg/KDb-1)*Fb*Fg+Fb*(F\text{ginf}-(KDg/KDb)*Fg0)+Fg(Fb0-(KDg/KDb)*F\text{binf})$$

where

GII is the glucose independent intensity;

Fb is the measured intensity of the first frequency component;

Fg is the measured intensity of the second frequency component;

KDg is the apparent dissociation constant determined when using only the second frequency component;

KDb is the apparent dissociation constant determined when using only the first frequency component;

Fginf is the intensity of the second frequency component at saturated concentration;

Fg0 is the intensity of the second frequency component at zero concentration;

Fbinf is the intensity of the first frequency component at saturated concentration; and Fb0 is the intensity of the first frequency component at zero concentration.

* * * * *